(12) United States Patent
Schmidt et al.

(10) Patent No.: US 12,266,100 B2
(45) Date of Patent: Apr. 1, 2025

(54) GENERATING X-RAY IMAGE DATA ON THE BASIS OF A WEIGHTING OF BASIS MATERIALS VARYING DEPENDING ON LOCATION

(71) Applicant: Siemens Healthcare GmbH, Erlangen (DE)

(72) Inventors: Bernhard Schmidt, Fuerth (DE); Thomas Allmendinger, Forchheim (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 413 days.

(21) Appl. No.: 17/677,216

(22) Filed: Feb. 22, 2022

(65) Prior Publication Data

US 2022/0270251 A1 Aug. 25, 2022

(30) Foreign Application Priority Data

Feb. 25, 2021 (DE) ..................... 10 2021 201 809.2

(51) Int. Cl.
G06T 7/00 (2017.01)
A61B 6/03 (2006.01)

(52) U.S. Cl.
CPC ............ *G06T 7/0012* (2013.01); *A61B 6/032* (2013.01); *G06T 2207/10081* (2013.01)

(58) Field of Classification Search
CPC ......... G06T 7/0012; G06T 2207/10081; G06T 2211/408; G06T 11/003; A61B 6/032; A61B 6/482
See application file for complete search history.

(56) References Cited

U.S. PATENT DOCUMENTS

| 9,330,440 B2 * | 5/2016 | Kwon | ..................... A61B 6/463 |
| 2009/0052612 A1 * | 2/2009 | Wu | ...................... A61B 6/5205 |
| | | | 378/5 |

(Continued)

FOREIGN PATENT DOCUMENTS

| DE | 102011083727 A1 | 4/2013 |
| DE | 102015223601 A1 | 6/2017 |

(Continued)

OTHER PUBLICATIONS

Skurowski, Przemystaw et al: "High dynamic range in x-ray imaging"; In: International Conference on Information Technologies in Biomedicine. Springer, Cham,; Year: 2018, pp.: 39-51.

(Continued)

*Primary Examiner* — Matthew C Bella
*Assistant Examiner* — Janice E. Vaz
(74) *Attorney, Agent, or Firm* — Harness, Dickey & Pierce, P.L.C.

(57) ABSTRACT

An imaging method is described for generating image data of an examination region of an object that is to be examined. First X-ray projection measurement data of the examination region is acquired using a first X-ray energy spectrum and at least second X-ray projection measurement data of the examination region is acquired using a second X-ray energy spectrum which is different from the first X-ray energy spectrum. A priori image data is reconstructed based on at least the first X-ray projection measurement data and a location-dependent distribution of X-ray attenuation values. A basis material decomposition is performed based on the first X-ray projection measurement data and the at least second X-ray projection measurement data. A location-dependent weighting of the basis materials is determined as a function of the location-dependent distribution of the X-ray attenuation values. An image for the examination (Continued)

region is determined by reconstructing virtual basis-material-weighted image data.

16 Claims, 6 Drawing Sheets

(56) References Cited

U.S. PATENT DOCUMENTS

| | | | |
|---|---|---|---|
| 2010/0131885 A1 | 5/2010 | Gabrielse et al. | |
| 2013/0083989 A1 | 4/2013 | Flohr et al. | |
| 2016/0307340 A1* | 10/2016 | Allmendinger | G06T 11/008 |
| 2017/0245816 A1* | 8/2017 | Flohr | A61B 6/481 |
| 2017/0301082 A1 | 10/2017 | Allmendinger et al. | |
| 2017/0303869 A1 | 10/2017 | Goshen | |
| 2020/0187872 A1 | 6/2020 | Flohr et al. | |
| 2021/0110583 A1 | 4/2021 | Lee et al. | |
| 2021/0267563 A1* | 9/2021 | Sattarivand | A61B 6/505 |

FOREIGN PATENT DOCUMENTS

| | | |
|---|---|---|
| DE | 102016203257 A1 | 8/2017 |
| DE | 102018221691 A1 | 6/2020 |
| EP | 3644282 A1 | 4/2020 |

OTHER PUBLICATIONS

Grant, K.L., et.al.: "Assessment of an Advanced Image-Based Technique to Calculate Virtual Monoenergetic Computed Tomographic Images From a Dual-Energy Examination to Improve Contrast-to-Noise Ratio in Examinations Using Iodinated Contrast Media" in: Investigative Radiology, 2014; 2014.

Macovski A. et al:"Energy-selective Reconstructions in X-ray Computerized Tomography", Phys. Med. Biol. 21, 733-744 (1976).

* cited by examiner

GENERATING X-RAY IMAGE DATA ON THE BASIS OF A WEIGHTING OF BASIS MATERIALS VARYING DEPENDING ON LOCATION

CROSS-REFERENCE TO RELATED APPLICATION(S)

The present application hereby claims priority under 35 U.S.C. § 119 to German patent application number DE 102021201809.2 filed Feb. 25, 2021, the entire contents of which are hereby incorporated herein by reference.

FIELD

Example embodiments are related to X-ray imaging methods for generating image data of an examination region or field of view (FOV) of an object that is to be examined. Example embodiments are further related to image data generating devices and computed tomography systems.

BACKGROUND

State-of-the-art imaging methods are often enlisted to aid in generating two- or three-dimensional image data which can be used for visualizing an imaged examination object as well as for further applications.

In many cases the imaging methods are based on the detection of X-ray radiation, with data referred to as projection measurement data being generated in the process. Projection measurement data can be acquired with the aid of a computed tomography system (CT system), for example. In CT systems, a gantry-mounted combination consisting of X-ray source and oppositely positioned X-ray detector typically rotates around a measurement chamber in which the examination object (which is referred to in the following without loss of generality as the patient in most cases) is situated. The center of rotation (also known as the "isocenter") coincides in this case with an axis referred to as system axis z. In the course of one or more revolutions, the patient is irradiated with an X-ray beam emitted by the X-ray source, during which process projection measurement data or X-ray projection measurement data is acquired with the aid of the oppositely mounted X-ray detector.

The generated projection measurement data is dependent in particular on the construction of the X-ray detector. X-ray detectors typically comprise a plurality of detection units, which are mostly arranged in the form of a regular pixel array. Each of the detection units generates a detection signal for X-ray radiation incident on the detection units, which signal is analyzed at specific time points in terms of the intensity and spectral distribution of the X-ray radiation in order to make inferences in relation to the examination object and to generate projection measurement data.

During CT examinations, the tube voltage is frequently adjusted in line with patient parameters, such as the patient's size and stature, for example, as well as according to the type of examination planned. For example, a native imaging scan without contrast agent can be performed or an examination of a parenchymal organ such as the liver can be conducted with contrast agent or a CT angiography method can be carried out.

In CT imaging with spectrally resolved CT data, generated for example through the use of photon-counting detectors, dual-source CT systems or CT systems having two X-ray beams, virtual monoenergetic image data is calculated with the aid of a multi-material decomposition, also known as a basis material decomposition. In this case a monoenergetic CT image reconstructed at a mean X-ray energy of 65 keV, for example, roughly corresponds to a 120-kV image using a conventional image reconstruction. Such a value for a mean X-ray energy is also referred to in the following as a keV value for short. The energy range for calculating such virtual monoenergetic image data lies approximately between 45 keV and 190 keV. The choice of the energy for calculating virtual monoenergetic image data can be used to calculate image series having different material contrasts and consequently to provide an improved basis for the subsequent diagnosis.

SUMMARY

An issue with the generation of such an image series is that in an image there is no globally generally valid keV value that could guarantee an optimal image quality in all subregions of such an image. For example, the contrast formation is regionally dependent on the respective organs. A favorable keV value for the liver, for example, is unfavorable for imaging the arterial vessels connected to the liver since there it generates much too high a contrast. For example, a value known as the window center/width value that is constant for the entire image leads to the vessels being "blanked" and lighting only as white. What is meant by this is that the X-ray attenuation values of the vessels, also called HU values for short, far exceed the maximum value of the X-ray attenuation values of the specified window.

Prior art practice entailed generating a large number of additional monoenergetic series, with the physician swapping back and forth between the series in the course of the diagnostic assessment of the images depending on the region in the image that is currently being evaluated. Alternatively, it is possible for images to be reconstructed by the CT system in a form which permits monoenergetic images to be calculated interactively at a workstation. In this way, an image presentation is adjusted during the diagnostic assessment by actuating a shifting element known as a "slider", which changes the keV value and triggers a recalculation of the image. Accordingly, the keV value can be readjusted by the physician as necessary. Admittedly, a high computational overhead must be accepted for the frequent recalculation of the images, which means that heavy demands are placed on the computer unit of the CT system. In most cases the physician must therefore wait a relatively long time when changing the keV value until the corresponding image has been recalculated and displayed to him or her.

The problem is therefore to disclose an X-ray imaging method as well as a corresponding image data generating device which enable a simplified visualization of images of extensive body regions while maintaining good image quality.

This object is achieved by an X-ray imaging method for generating image data of an examination region of an object to be examined, an image data generating device and a computed tomography system according to example embodiments.

At least one example embodiment provides an X-ray imaging method, such as a CT X-ray imaging method, for generating image data of an examination region of an object to be examined, first X-ray projection measurement data is acquired initially using a first X-ray energy spectrum and at least second X-ray projection measurement data of the examination region of an examination object is acquired using a second X-ray energy spectrum, the second X-ray energy spectrum being different from the first X-ray energy spectrum.

The X-ray projection measurement data can be received for example by a data storage device of a computed tomography system or of a data network of a clinic system. Alternatively, the X-ray projection measurement data can also be obtained directly within the scope of a CT measurement method and processed further a method according at least one example embodiment. In this case the X-ray projection measurement data can be acquired for example using what is termed a multi-energy measurement method, preferably a dual-energy measurement method, in which X-ray beams having different X-ray energy spectra are emitted in the direction of a region that is to be examined, are partially absorbed by said region, and the transmitted fraction of the X-ray beams is subsequently detected by different X-ray detectors.

The X-ray detectors may be spectrally resolving, though this is not an essential requirement. In the dual-source case, a method in which two separate X-ray sources operating at different X-ray energies are used, or the kV-switching case, in which the electrical voltage of the X-ray source is switched over between different values, conventional X-ray detectors are used even today. Here, the acquisition is performed using different X-ray energy spectra. Alternatively, the spectral data can also be acquired using a spectrally resolving X-ray detector. In this case the acquisition using only one X-ray beam with a single X-ray energy spectrum is then sufficient. The energy separation is achieved in this case at the X-ray detector, in contrast to the aforementioned methods, in which X-ray beams are emitted with different X-ray energy spectra. Generally, however, it is also possible to combine these methods with a spectral X-ray detector.

Furthermore, a priori image data is reconstructed on the basis of at least the first X-ray projection measurement data. Alternatively, a composite image corresponding to a conventional CT image or a native (pre-contrast) image can also be generated from the first and the second X-ray projection measurement datasets. In such a composite image, the image data of different X-ray spectra are typically merged with approximately equal weighting. Such a composite image typically corresponds to a 120-kV image which is optimized for the contrast of water, in particular insofar as the contrast-to-noise ratio is concerned. Said a priori image data is therefore generated prior to the actual multienergetic image reconstruction in preparation for the subsequent image reconstruction.

A location-dependent distribution of X-ray attenuation values in the examination region is then determined on the basis of the reconstructed a priori image data. For this purpose, regional X-ray attenuation values can be determined, for example, for individual subregions of the examination region. At the same time, individual subregions, each having a limited bandwidth of attenuation values, are preferably identified and segmented. In the extreme case, each of said subregions may also comprise only one image element or image pixel. The regional bandwidths of attenuation values assigned to the individual subregions then serve as a point of reference for determining, in the wake of a basis material decomposition on the basis of the first X-ray projection measurement data and the at least second X-ray projection measurement data, a location-dependent or regionally specific weighting of the basis materials as a function of the determined location-dependent distribution of the X-ray attenuation values that is used for a reconstruction of image data on the basis of the basis material decomposition. Finally, an overall image is generated for the examination region by reconstructing location-dependent virtual basis-material-weighted image data, weighted differently regionally, for example, and combining the same in the cited overall image. For this purpose, partial images containing location-specific partial image data can be generated initially by reconstructing virtual basis-material-weighted image data, weighted differently depending on location, and finally the overall image can be generated by combination of the partial image data.

A method for reconstructing or calculating virtual basis-material-weighted image data, in particular pseudo-monoenergetic image data, is known from Alvarez R. E. and Macovski A. "Energy-selective reconstructions in x-ray computed tomography", Phys. Med. Biol. 21, 733-744 (1976), the entire contents of which are incorporated by reference.

A particularly suitable method for reconstructing or calculating image data reconstructed in such a way, in particular pseudo-monoenergetic image data, is described in K. L. Grant et al. "Assessment of an Advanced Image-Based Technique to Calculate Virtual Monoenergetic Computed Tomographic Images from a Dual-Energy Examination to Improve Contrast-To-Noise Ratio in Examinations Using Iodinated Contrast Media", Investigative Radiology 2014; 00: 00-00, the entire contents of which are incorporated by reference.

Filtering and smoothing methods can be used in the reconstruction and combination of the differently reconstructed image data in order in particular to harmonize the transition zones between the individual subregions or to reduce noise effects.

Such a locally optimized image generation using different weighting in the weighting of the basis materials, for example through the location-dependent or region-dependent use of so-called keV levels, enables an improved visualization of extremely different material contrasts in a single image. Advantageously, a medical practitioner can conduct the complete diagnostic assessment on the basis of a single image series and does not have to switch back and forth between different reconstructions. Furthermore, the number of images necessary for an examination is reduced, which saves on resources in relation to the computing time for the image reconstruction, the storage space used for the image data and the management of the image data. The keV values can also be varied continuously. In this way, artifacts due to discontinuities in the variation of the keV values can be avoided.

At least one example embodiment provides an image data generating device that has a control unit for actuating one or more X-ray sources of a CT system in such a way that X-ray beams are generated with a first X-ray energy spectrum and a second X-ray energy spectrum which is different from the first X-ray energy spectrum. Preferably, the different X-ray energy spectra are generated for this purpose in each case at a first or a second mean energy. The two energy values can be preset default values.

The image data generating device additionally comprises a projection measurement data acquisition unit for acquiring first X-ray projection measurement data and at least second X-ray projection measurement data of an examination region of an examination object using the first X-ray energy spectrum and the second X-ray energy spectrum, respectively.

Also part of the image data generating device is a preliminary image reconstruction unit for reconstructing a priori image data on the basis of at least the first X-ray projection measurement data.

The image data generating device additionally comprises a value determination unit for determining a location-dependent distribution of X-ray attenuation values in the examination region.

The image data generating device additionally comprises a weighting unit for determining a location-dependent weighting of the basis materials as a function of the location-dependent distribution of the X-ray attenuation values. For this purpose, a suitable third X-ray energy spectrum is preferably determined having a regionally specific, suitable third mean energy, preferably a single third energy value, also referred to as a keV value, on the basis of a regional X-ray attenuation value determined in each case, in which event said third X-ray energy spectrum or the mean energy can be used for a weighting in a reconstruction of basis-material-weighted image data.

During the reconstruction on the basis of basis materials, it is also possible to use a spectrally variable weight instead of a constant weight. The weight can be determined as an arbitrary functional relationship $w=f(E(keV), x, y)$, where x, y are spatial coordinates and E is a spectral energy in the unit keV. Instead of a multiplication of the weight by the respective X-ray attenuation of the basis material fractions, it is also possible for example to perform a convolution of a spectrally variable weight with a spectrally resolved X-ray attenuation. For this, a spectrally highly resolving X-ray counting detector would be necessary. An improved accuracy of the reconstruction, possibly with even fewer artifacts, can be achieved.

Also part of the image data generating device is an image generating unit for generating an overall image for the examination region by reconstructing virtual basis-material-weighted image data weighted differently depending on location. Preferably, regional, preferably pseudo-monoenergetic, image data assigned to the respective third X-ray energy spectrum having the respective third mean energy, preferably a single third energy value, is reconstructed region by region on the basis of the acquired first and at least second X-ray projection measurement data. The regionally reconstructed image data is combined into an overall image by the image generating unit. For this purpose, the function of the image generating unit can also be subdivided into a partial image generating unit and an overall image generating unit. Initially, the partial image generating unit generates partial images with location-specific partial image data by reconstructing virtual basis-material-weighted image data weighted differently depending on location, and finally the overall image generating unit generates the overall image by combining the partial image data. The image data generating device shares the advantages of the X-ray imaging method.

The computed tomography system comprises an image data generating device according to at least one example embodiment. The image data generating device can in particular be part of a control device of the computed tomography system. The computed tomography system shares the advantages of the image data generating device.

Most of the main components of the image data generating device can be embodied in the form of software components. This relates in particular to the preliminary image reconstruction unit, the value determination unit, the decomposition unit, the weighting unit, and the image generating unit. In principle, however, some of these components may also be realized in the form of software-assisted hardware, for example FPGAs or the like, in particular when there is a requirement for particularly fast calculations. Similarly, the interfaces may be embodied as software interfaces, for example when it is simply a matter of importing data from other software components. They may, however, also be embodied as hardware-based interfaces which are controlled by suitable software.

A largely software-based implementation has the advantage that computer units or control devices of computed tomography systems already in use previously in the prior art can also be easily upgraded by a software update in order to operate in the manner according to at least one example embodiment. In that respect, the object is also achieved by a corresponding computer program product comprising a computer program which can be loaded directly into a memory device of a computer unit or a control device of a computed tomography system (e.g., one or more processors or other processing circuitry) and having program sections for the purpose of performing all the steps of the method when the computer program is executed in the computer unit or control device of the computed tomography system.

As well as the computer program, such a computer program product may, where appropriate, comprise additional constituent parts such as e.g. a set of documentation and/or additional components, including hardware components, such as e.g. hardware keys (dongles, etc.) to allow use of the software.

A computer-readable medium, for example a memory stick, a hard disk or some other transportable or permanently installed data carrier, on which the program sections of the computer program that can be read in and executed by a computer unit are stored, may be used for transporting the computer program product to the memory device of a computer unit of a computed tomography system and/or for storing the same on the computer unit of the computed tomography system. For this purpose, the computer unit may have e.g. one or more cooperating microprocessors or the like.

At least one example embodiment provides an image data generating device including processing circuitry configured to control one or more X-ray sources of a CT system in such a way that X-ray beams are generated using a first X-ray energy spectrum and a different second X-ray energy spectrum, acquire first X-ray projection measurement data of an examination region of an examination object using the first X-ray energy spectrum and at least second X-ray projection measurement data using the second X-ray energy spectrum, reconstruct a priori image data on the basis of at least the first X-ray projection measurement data, determine a location-dependent distribution of X-ray attenuation values in the examination region on the basis of the first X-ray projection measurement data, perform a basis material decomposition on the basis of the first X-ray projection measurement data and the at least second X-ray projection measurement data, determine a location-dependent weighting of the basis materials as a function of the location-dependent distribution of the X-ray attenuation values and generate an overall image for the examination region by reconstructing virtual basis-material-weighted image data weighted differently depending on location.

The dependent claims and the following description in each case contain particularly advantageous embodiments and developments of example embodiments. In particular, the claims of one claims category can at the same time also be developed analogously to the dependent claims of a different claims category. Furthermore, the various features of different exemplary embodiments and claims may also be combined within the scope of example embodiments to create new exemplary embodiments.

Determining a location-dependent weighting preferably comprises an automated determination of a suitable third X-ray energy spectrum having a regionally specific, suitable third mean energy, preferably a single third energy value, on the basis of the determined location-dependent distribution of the X-ray attenuation values. Said third mean energy value or a keV value assigned to said value then serves a basis for the respective reconstruction of regional, preferably pseudo-monoenergetic, image data in the individual segments or regions. The image data is reconstructed on the basis of the first and at least second X-ray projection measurement data acquired using the respective third X-ray energy spectrum with the respective third mean energy, preferably a single third energy value. Said third energy value or the third X-ray energy spectrum can now be different for each segment or each region and is advantageously adjusted to fit the contrast behavior or the HU values in the respective region in order to improve the local image quality in the individual subregions or segments of the examination region. Advantageously, information known in advance about the relationship between the X-ray attenuation values and a keV value suitable for an optimal image quality or an X-ray energy spectrum suitable therefor is used for choosing the third X-ray energy spectrum. Details in this regard are explained further below.

The third X-ray energy spectrum preferably comprises a single X-ray energy. In other words, a monoenergetic X-ray energy spectrum is preferably available as the third X-ray energy spectrum, the third "mean" energy then representing the single energy of the monoenergetic X-ray energy spectrum. Particularly preferably, when reference is made in the following to a third X-ray energy spectrum having a third mean energy, it should also always include therein the special embodiment variant in which pseudo-monoenergetic X-ray images are generated on the basis of a single energy; the "mean" energy then corresponds to said single energy value or keV value.

During the generation of virtual monoenergetic image data, also known as pseudo-monoenergetic image data, a decomposition of the acquired projection measurement data is performed in the raw data space or a decomposition of the image data reconstructed therefrom is performed in the image data space. For example, when an iodinated contrast agent is used, the data is decomposed into an iodine/calcium component and into a water/soft tissue component, and an attenuation value (HU value) is then calculated for the respective voxel based on density values with the aid of tabulated values for an X-ray energy value (keV value) chosen by the user. Preferably, the acquired first and/or second projection measurement data is projection measurement data generated in the presence of a contrast agent. For example, a blood vessel or a blood-saturated tissue component can be made particularly clearly visible by a contrast agent.

In one embodiment of the X-ray imaging method, the location-dependent third energy value or keV value is determined by applying a lookup table to the determined location-dependent distribution of the X-ray attenuation values in the a priori image data. Advantageously, the relationship between the keV value and the distribution of the X-ray attenuation values can be determined experimentally or in a model-based manner and stored in a table which can be accessed at any time without computational overhead or further experimental overhead.

Alternatively, the location-dependent third energy value can be determined using a target function which maps X-ray attenuation values to suitable keV values. Such a target function can be determined empirically, for example. Advantageously, the relationship between the determined X-ray attenuation values and the keV values can be determined theoretically or in a model-based manner without experimental procedures.

Particularly advantageously, the respective third energy value or keV value is chosen in such a way that an improved contrast-to-noise ratio is achieved compared to an image visualized at the first or second energy value.

Individual imaged organ regions are preferably segmented and classified in the a priori image data. A specific basis material weighting is then specified in each case as a function of the different location-dependent distribution of the X-ray attenuation values in the different segments. In this process, a regionally specific, suitable third mean energy can be determined for example as a function of the classification of the individual segments by organ types. For the overall image, virtual basis-material-weighted image data weighted on a segment-specific basis in each case is then reconstructed. Advantageously, prior known information about the optimal visualization of different organs can be used in the choice of the third mean energy. It is known, for example, that the liver can be visualized in a particularly detailed and high-contrast manner at values of the mean energy of 45 keV, the kidneys at values of 55 keV, the arteries at values of 70 keV, and the veins at values of 65 keV.

In addition to the attenuation values, spectral information can also be incorporated into the reconstruction of the virtual basis-material-weighted image data. The spectral information can be used in particular in addition to the a priori image data for the purpose of determining a regionally specific, suitable third mean energy. This information can be made available for example in the form of a metric known as a dual-energy ratio. Advantageously, the spectral information can be used to identify special materials foreign to the body in the examination region, for example materials of prostheses, and to specify a regionally specific, suitable third mean energy as a function of the identified materials in order thereby to reduce image artifacts which are caused in particular by metallic parts in the body of a patient. For example, vascular stents can be identified in a coronary angiography examination. Typically, metals either generate artifacts or negatively influence the image impression, so high keV values are not desirable in the image areas occupied by metals.

During the reconstruction of virtual basis-material-weighted image data, weighted on a segment-specific basis, the third energy value is preferably varied continuously depending on location in at least one segment and a continuous transition of the third energy values or keV values is produced in a border zone between at least two segments by approximation of the third energy values of the two segments to one another in the border zone.

This approach acts like a smoothing method on the transitions between the individual regions or segments. This results in a compensation of the division of the examination region into segments so that no abrupt changes occur between the individual mean energy values, and consequently also the image contrasts, in particular in the transition zones between the individual segments. Advantageously, the image quality is improved further as a result of this type of modification.

In the reconstruction of virtual basis-material-weighted image data weighted differently depending on location, at least one of the following material decompositions can advantageously be applied:

a material decomposition into iodine and water,
    a material decomposition for a virtual non-contrast image
    a material decomposition for a virtual non-calcium image,
    a combination of regionally different material decompositions for different regions of the examination region.

A material decomposition into iodine and water permits the clear visualization of blood vessels dosed with contrast agents.

A material decomposition for a virtual non-contrast image comprises a material decomposition into iodine and water, the virtual non-contrast image then being reconstructed by suitable weighting on the basis of said basis materials. The non-contrast image corresponds in this case to the water component of the basis materials.

A material decomposition for a non-calcium image comprises firstly a decomposition into iodine and calcium. Next, the calcium image is subtracted from a standard composite image, as has already been described above, resulting in an image without calcium components. Advantageously, structures hidden or overshot by the very dense, strongly absorbing calcium are more clearly visible.

A combination of regionally different material decompositions for different segments of the examination region permits a particularly effective adjustment of the image reconstruction to fit regional material distributions.

In a special variant of the X-ray imaging method, a highest possible energy value is chosen as the third mean energy value in low-density regions for the case where a scan is performed without contrast agent. With this approach, beam hardening artifacts and metal artifacts can advantageously be reduced. Since no contrast agent is used in this case, choosing a lower mean energy also does not lead to a better contrast-to-noise ratio. It is therefore advantageous in this case to use a higher third mean energy value or keV value for generating pseudo-monoenergetic image data with which the cited artifacts are reduced and thus an improvement in image quality is achieved.

BRIEF DESCRIPTION OF THE DRAWINGS

Example embodiments are explained again in more detail below with the aid of exemplary embodiments and with reference to the attached figures, in which.

DETAILED DESCRIPTION

Figure 1:
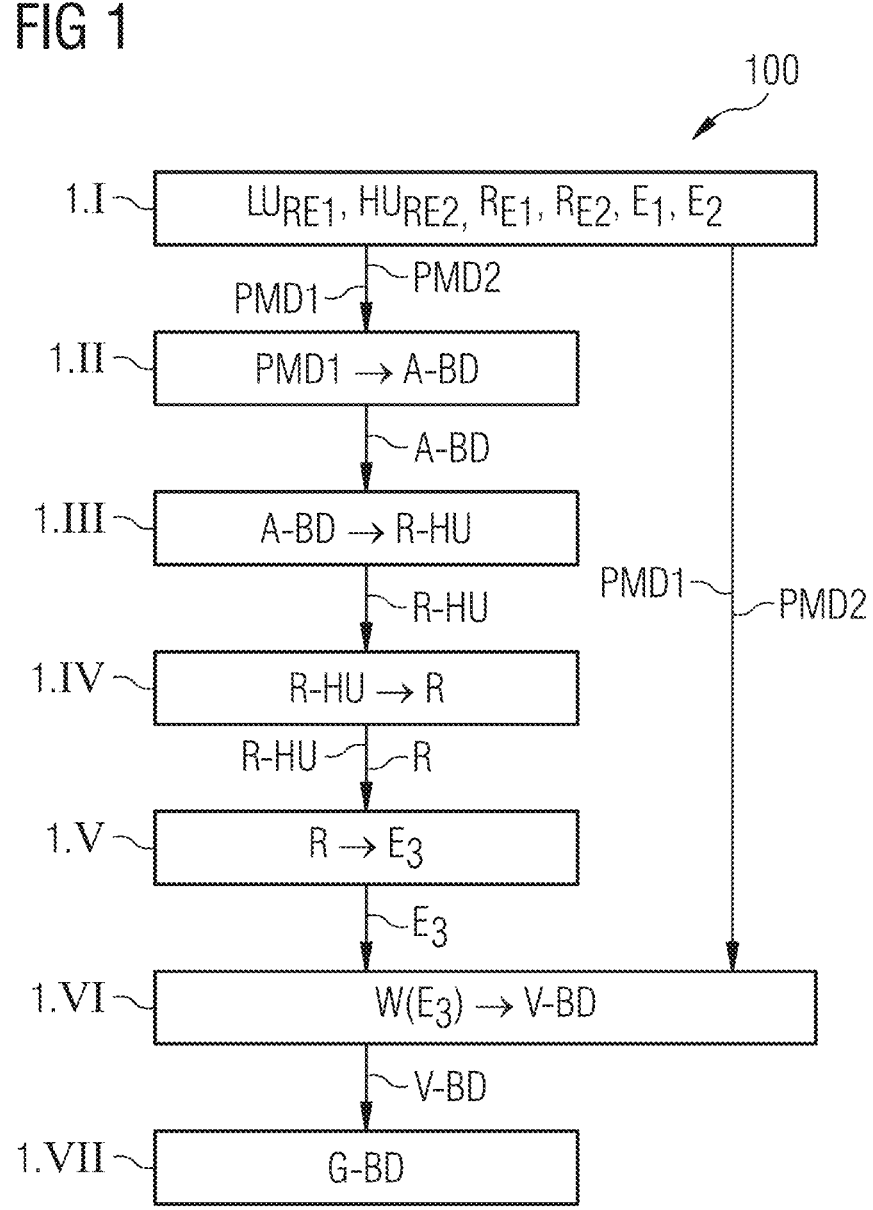
FIG. 1 shows a flowchart illustrating an X-ray imaging method according to at least one example embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one example embodiment, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

FIG. 1 shows a flowchart 100 illustrating a CT imaging method with the aid of the technique known as dual-energy CT, in which contrast-enhanced image data of a patient is generated, according to an exemplary embodiment of the invention.

In an imaging method with the aid of the dual-energy technique, two projection measurement datasets PMD1, PMD2 are acquired, each of which is generated by X-ray beams having different X-ray energy spectra RE1, RE2 with different mean energy values E1, E2. To generate the X-ray beams with different X-ray energy spectra RE1, RE2, two X-ray sources 15a, 15b (see FIG. 3) can be used, for example, which emit X-ray beams having different mean X-ray energy values E1, E2 or X-ray energy spectra RE1, RE2.

Within the scope of the imaging method, X-ray beams having different first and second X-ray energy spectra RE1, RE2 are initially generated at step 1.I by two different X-ray sources. Said X-ray energy spectra RE1, RE2 are generated with the aid of a relatively low first tube voltage LURE1 of 80 kV and a relatively high second tube voltage HURE2 of 150 kV. The X-ray tubes of the X-ray sources are excited with the aid of the first and second tube voltages LURE1 and HURE2 into generating X-ray beams with predetermined first and second mean energy values E1, E2. The mean energy values E1, E2 of the thus generated X-ray spectra amount to approx. 45 keV for the first X-ray energy spectrum RE1 and approx. 80 keV for the second X-ray energy spectrum RE2. Also at step 1.I, the X-ray beams generated by the two X-ray sources are detected by two X-ray detectors 16a, 16b (see FIG. 3) mounted opposite the respective X-ray sources. This imaging method, also known as a dual-energy CT measurement method, is used in the method applied in FIG. 1 for generating first and second projection measurement datasets PMD1, PMD2, which are assigned to the respective different X-ray energy spectra RE1, RE2.

At step 1.II, a priori image data A-BD is then reconstructed on the basis of the first X-ray projection measurement data PMD1 that was acquired at the lower first energy E1=45 keV. The reconstruction of the a priori image data A-BD involves considerably less overhead than a reconstruction on the basis of both image datasets PMD1, PMD2.

Figure 4:
FIG. 4 shows an a priori X-ray image of a patient torso.

At step 1.III, regional X-ray attenuation values R-HU are determined in the examination region on the basis of the a priori image data A-BD. A visualization of a CT image acquisition of a patient torso at a low energy of 45 keV is shown in FIG. 4. Such an image is suitable as a basis for a subsequent segmentation as a function of occurring HU values and artifacts. Particularly weakly absorbing regions such as the lung, for example, are also clearly recognizable therein.

At step 1.IV, a segmentation of the examination region is carried out on the basis of the determined X-ray attenuation values R-HU. In this case the segments or regions R are specified and classified according to the determined X-ray attenuation values.

Figure 5:
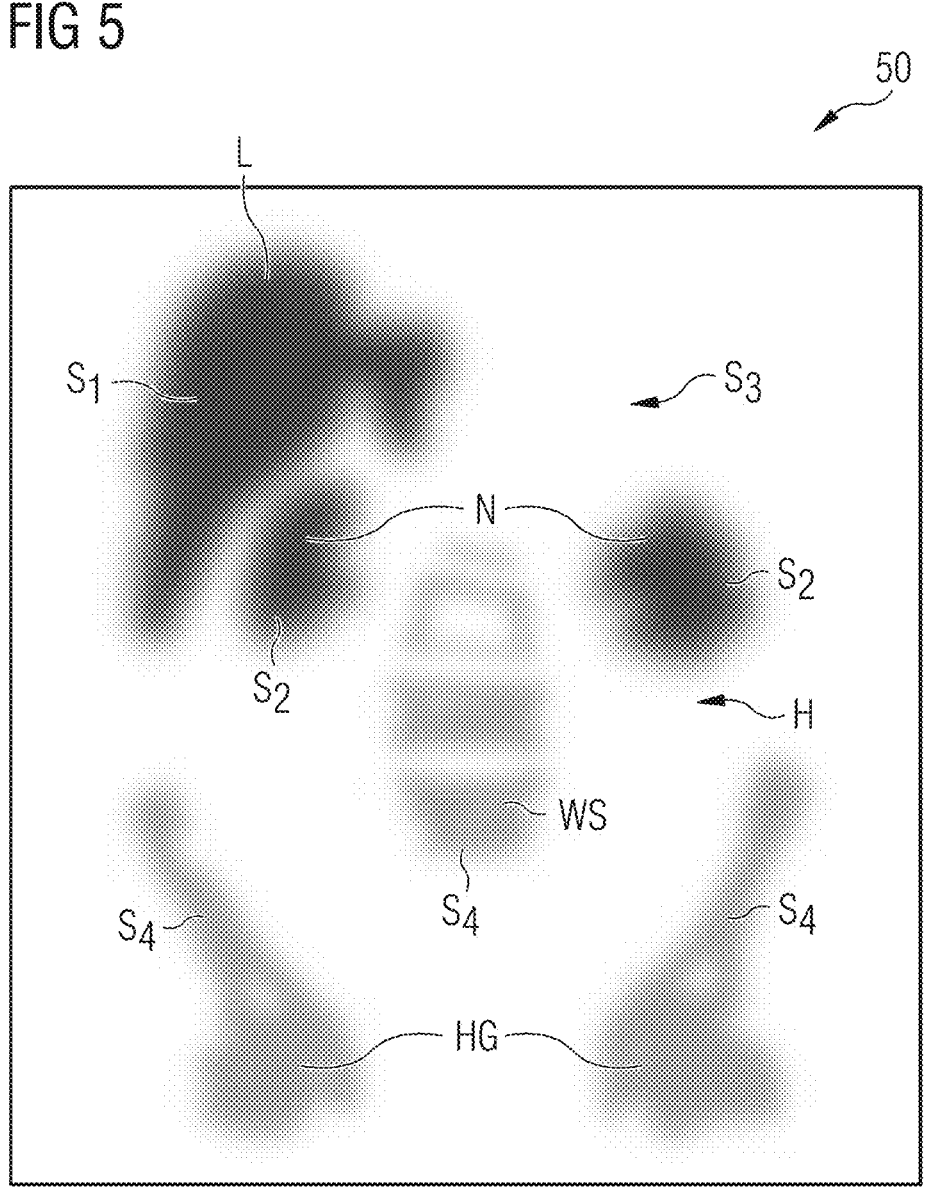
FIG. 5 shows a target keV image generated on the basis of the a priori image shown in FIG. 4.

Next, at step 1.V, a suitable third X-ray energy spectrum RE3 having a regionally specific suitable third mean energy E3 or a corresponding keV value is specified automatically for each of the regions on the basis of the regional X-ray attenuation values R-HU determined in each case. In this particular example, the specification is accomplished by applying a lookup table which correlates the determined regional HU values R-HU with suitable keV values for an image reconstruction. Alternatively, the segments can also be specified on an organ-specific basis and organ-specific keV values can be determined for the individual organs. For this purpose, a target keV image is generated on the basis of the a priori image data A-BD, as illustrated in FIG. 5.

At step 1.VI, virtual monoenergetic image data V-BD is then reconstructed with a segment-specific weighting W(E3) for the individual segments using the target keV values E3 determined in each case on the basis of the acquired first and second X-ray projection measurement data PMD1, PMD2.

Finally, at step 1.VII, an overall image G-BD is generated on the basis of the regional virtual monoenergetic image data V-BD.

Furthermore, a strong smoothing of the image data is performed on the border zones between the individual segments or regions R in order to reduce severe noise and/or abrupt changes between the individual target keV values or energies E3 in these image areas.

It is important here that no smoothing of the individual partial images is performed or planned, but that this smoothing, and hence the smooth transitions, relates only to the weighting function W(E3) that binds the individual parts together. This can also be regarded as a characteristic of the weighting function that the latter is sufficiently smooth.

Figure 2:
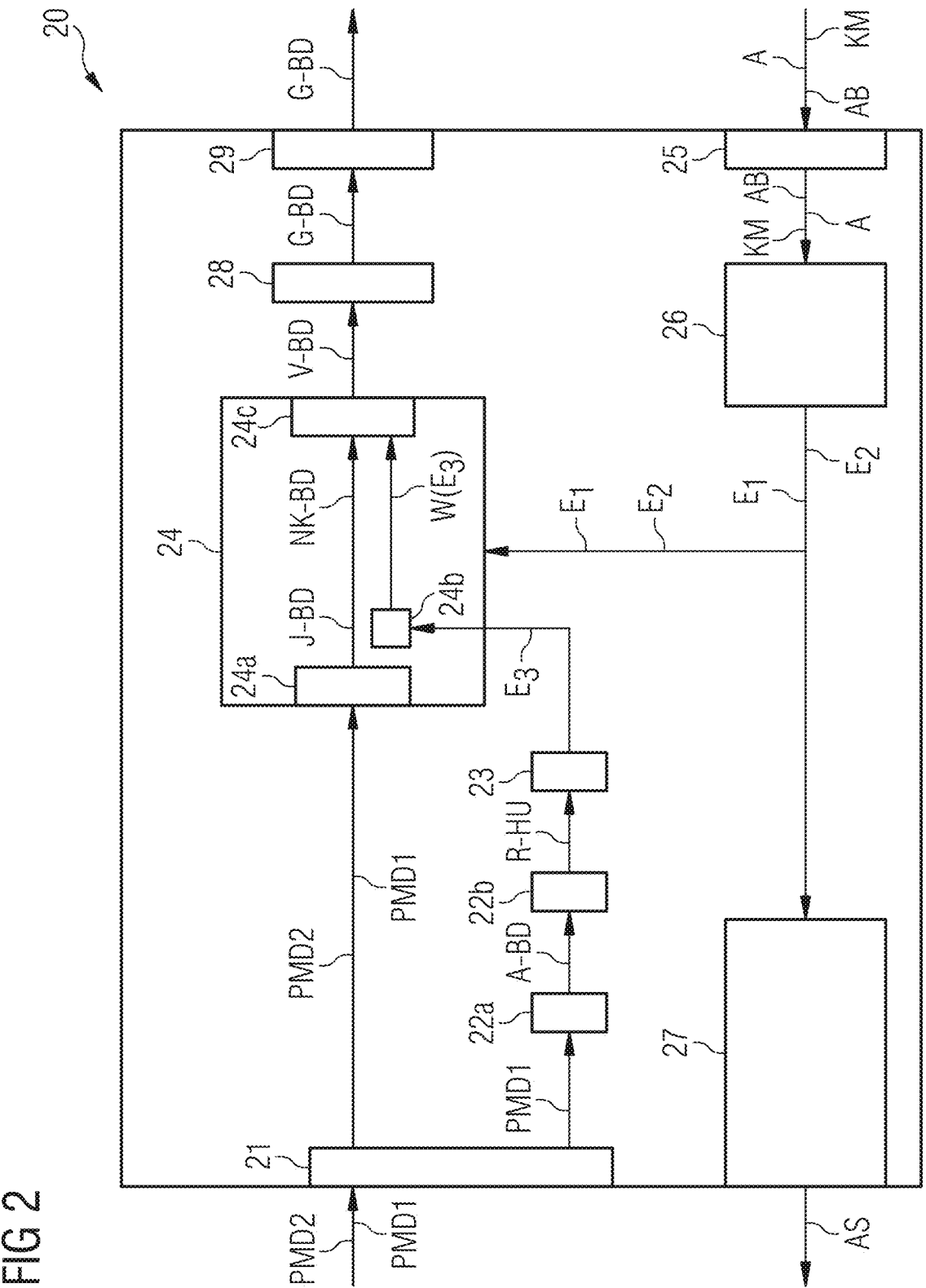
FIG. 2 shows a block diagram illustrating an image data generating device according to at least one example embodiment.

FIG. 2 shows a schematic view of an image data generating device 20 according to an exemplary embodiment of the invention.

The image data generating device 20 comprises an input interface 25 via which information relating to the absorption behavior of a region to be examined FOV of a patient, in particular dimension parameter values A, is acquired, as well as information regarding the type of imaging method AB applied and the contrast agent KM administered in advance to the patient prior to an imaging method. The acquired data A, AB, KM is transmitted from the input interface 25 to an energy spectrum determination unit 26.

On the basis of the input keV values, the energy spectrum determination unit 26 determines corresponding mean energy values E1, E2 of a first X-ray energy spectrum RE1 and a second X-ray energy spectrum RE2 with the aid of an auto-keV algorithm.

Figure 3:
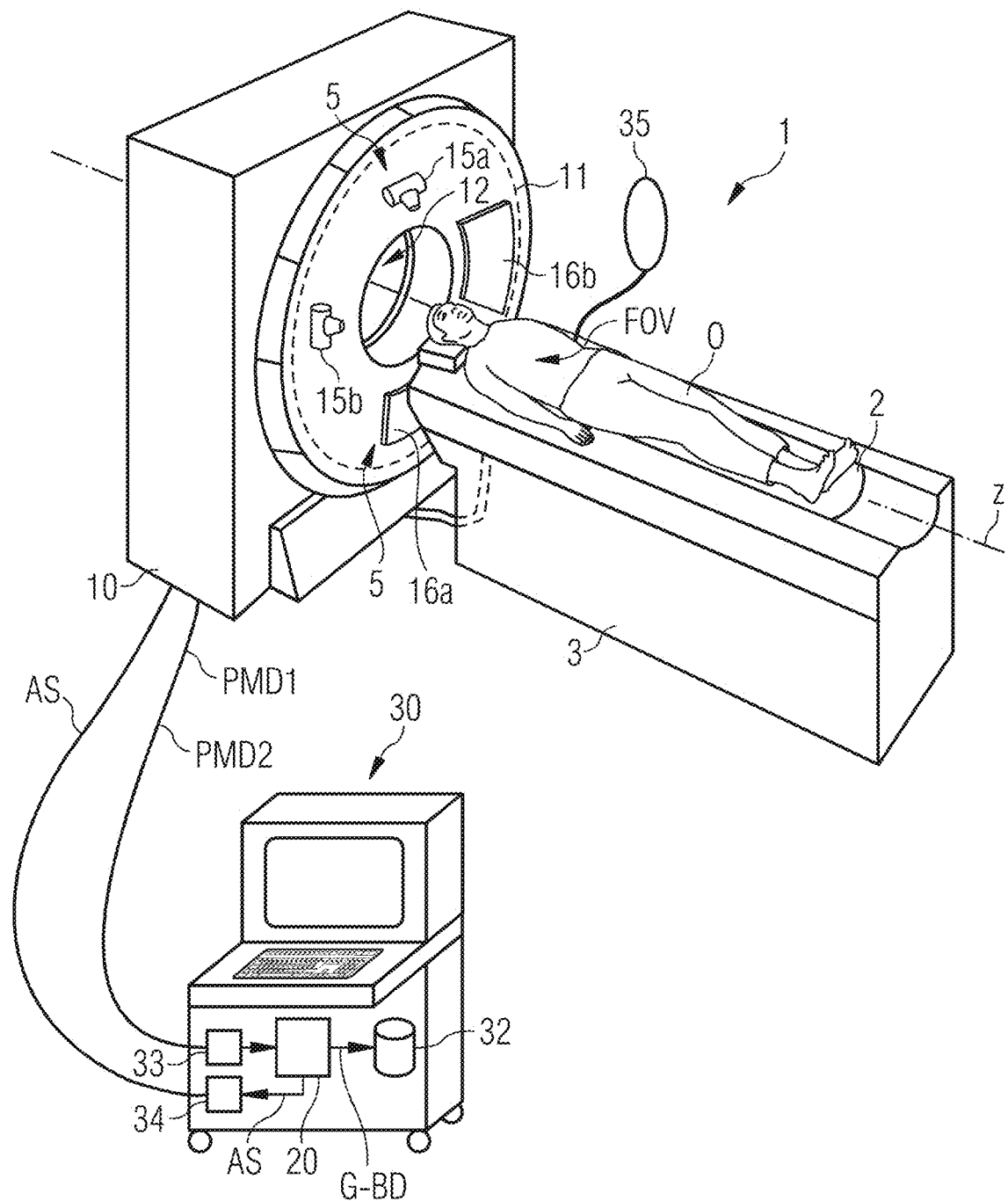
FIG. 3 shows a schematic view of a computed tomography system according to at least one example embodiment.

On the basis of the received energy values E1, E2, a control unit 27, which is likewise part of the image data generating device 20, now generates control signals AS which are forwarded to a control interface 34 (see FIG. 3) of the associated CT system 1 (see FIG. 3). In addition, the values determined for the first and second mean energies E1, E2 are relayed to a reconstruction unit 24 (which is still to be explained).

The image data generating device 20 shown in FIG. 2 also comprises a projection measurement data acquisition unit 21. The projection measurement data acquisition unit 21 serves for acquiring X-ray projection measurement data PMD1, PMD2 of an examination region FOV of an examination object O using different X-ray energy spectra RE1, RE2 during the actual imaging process or else from a database in which the X-ray projection measurement data PMD1, PMD2 has been stored. To generate the X-ray projection measurement data PMD1, PMD2, X-ray beams having first and second X-ray energy spectra RE1, RE2 are applied to the examination region FOV during the imaging process and the transmitted X-ray beams are detected by separate X-ray detectors (see detectors 16a, 16b in FIG. 3). The X-ray projection measurement data PMD1, PMD2 generated by the X-ray detectors and acquired by the projection measurement data acquisition unit 21 are then forwarded to the already mentioned image data reconstruction unit 24, which is subsequently intended to reconstruct pseudo-monoenergetic image data V-BD therefrom. The first X-ray projection measurement data PMD1 is also transmitted in addition to a preliminary image reconstruction unit 22a, which is configured to reconstruct a priori image data A-BD on the basis of the first X-ray projection measurement data PMD1. The a priori image data A-BD is forwarded to a value determination unit 22b, which is configured to determine regional X-ray attenuation values R-HU for individual segments in the examination region FOV. The regional X-ray attenuation values R-HU are forwarded to an energy value determination unit 23, which is configured to determine a keV value E3 for each segment on the basis of the regional X-ray attenuation values R-HU determined for each of the individual segments.

The determined mean keV values E3 are transmitted to the already mentioned reconstruction unit 24. The reconstruction unit 24 comprises a decomposition unit 24a, which performs a basis material decomposition on the basis of the acquired first and second X-ray projection measurement data PMD1, PMD2, first and second X-ray attenuation values being determined in each case for the basis materials, for iodine and water, for example. The first X-ray attenuation values are used to generate a sort of iodine map J-BD, and a non-contrast image NK-BD is generated with the second X-ray attenuation values. Also part of the reconstruction unit 24 is a weighting unit 24b, which now determines, for each segment or each of the keV values E3 assigned to the individual segments, a weighting factor W(E3) with which the X-ray attenuation values of individual basis materials or the iodine map J-BD and the non-contrast image NK-BD are subsequently to be weighted.

An associated weighting factor can be calculated from the keV value E3 by using a Physics-NIST table. This is a lookup table which establishes the physical relationship between keV value and weight. This relationship can be calculated from the material decomposition and the associated energy effects of Compton effect scattering versus photoelectric effect scattering.

The weighting factor W(E3) is forwarded to a partial image generating unit 24c, which is likewise part of the reconstruction unit 24 and generates regional virtual monoenergetic image data V-BD by weighted combination of the X-ray attenuation values of the iodine map J-BD and the non-contrast image NK-BD.

The regional virtual monoenergetic image data V-BD is therefore generated according to the following formula:

$$I_{V-BD} = W(E_3) \cdot I_{J-BD} + (1 - W(E_3)) \cdot I_{NK-BD}. \quad (1)$$

Here, the weighting W(E3) is a function of a virtual energy E3 or of the keV value and the X-ray attenuation values IV-BD, IK-BD, INK-BD are the X-ray attenuation values of the regional virtual monoenergetic image data V-BD, the iodine map data J-BD and the non-contrast image data NK-BD. The reconstruction unit 24 comprises a filter function and a smoothing function via which the weighting factors W(E3) or the keV values E3 are adjusted in such a way that border zones between the individual segments are harmonized and noise effects are reduced. In other words, the keV values E3 may also vary within a segment. For example, the keV values E3 of adjoining segments may approximate to one another at the border lines or boundaries of the segments, with the result that artifacts caused by abrupt changes in the keV values E3 in the border zones of the segments can be avoided.

A filter method is described in DE 10 2011 083 727 A1. Filter methods for reducing noise in X-ray images are also described in the applications filed with the German Patent and Trade Mark Office under the application numbers 10 2015 223 601.4 and 10 2015 223 606.4.

The regionally reconstructed image data V-BD is forwarded to an overall image generating unit 28, which is configured to generate an overall image G-BD on the basis of the regional virtual monoenergetic image data V-BD.

The combined and filtered, largely denoised overall image data G-BD is subsequently forwarded to an output interface 29, from which the overall image data G-BD is output for example to a data storage unit (see FIG. 3, data storage unit 32) or transferred to a display unit on which it is visualized as an image.

FIG. 3 shows a computed tomography system 1, called CT system 1 for short, which comprises the image data generating device 20 shown in FIG. 2. The CT system 1, which is embodied as a dual-energy CT system, essentially consists here of a conventional scan unit 10 in which a projection measurement data acquisition unit 5 comprising two X-ray detectors 16a, 16b and two X-ray sources 15a, 15b disposed opposite the detectors 16a, 16b rotates on a gantry 11 around a measurement chamber 12. Positioned in front of the scan unit 10 is a patient support and positioning device 3 or patient table 3, the upper part 2 of which, with a patient O disposed thereon, can be maneuvered toward the scanner 10 in order to move the patient O through the measurement chamber 12 relative to the detector system 16a, 16b. The scan unit 10 and the patient table 3 are controlled by a control device 30 from which acquisition control signals AS are emitted via a conventional control interface 34 in order to control the entire system in the conventional manner in accordance with predefined scanning protocols. In the case of a spiral acquisition, a movement of the patient O along the z-direction, which corresponds to the system axis z lengthwise through the measurement chamber 12, and the simultaneous rotation of the X-ray sources 15a, 15b relative to the patient O during the measurement result in a helical trajectory for the X-ray sources 15a, 15b. In the process, the detectors 16a, 16b constantly co-rotate in parallel opposite the X-ray sources 15a, 15b in order to acquire projection measurement data PMD1, PMD2, which is then used for reconstructing volume and/or slice image data. Similarly, a sequential measurement method can also be performed in which the patient table is advanced to a fixed position in the z-direction and then the projection measurement data PMD1, PMD2 is acquired at the relevant z-position during one revolution, a partial revolution or several revolutions in order to reconstruct a slice image at said z-position or in order to reconstruct image data from the projection measurement data of a plurality of z-positions. The method is basically also suitable for use on other CT systems, e.g. systems having just a single X-ray source and an oppositely mounted X-ray-counting detector or having a single X-ray source with a kV switching function or an X-ray detector forming a complete ring. The method can, for example, also be applied to a system having a stationary patient table and a gantry moving in the z-direction (also known as a sliding gantry).

The projection measurement data PMD1, PMD2 acquired by the detectors 16a, 16b (also referred to in the following as raw data) is transferred to the control device 30 via a raw data interface 33. Following suitable preprocessing where applicable, said raw data is then processed further in an image data generating device 20, which in the present exemplary embodiment is realized in the form of software on a processor in the control device 30. On the basis of the raw data PMD1, PMD2, said image data generating device 20 reconstructs overall image data G-BD with the aid of the method. The precise construction of such an image data generating device 20 is illustrated in detail in FIG. 2.

The overall image data G-BD generated by the image data generating device 20 is then stored in a data storage unit 32 of the control device 30 and/or output in the usual way on the screen of the control device 30. Said data can also be fed via an interface (not shown in FIG. 3) into a network connected to the computed tomography system 1, for example a radiological information system (RIS), and stored in a mass storage device that is accessible there or output as images on printers or filming stations connected there. The data can thus be processed further in any desired manner and then stored or output. Suitable control parameters or control signals AS are also determined via the image data generating device 20 on the basis of data input in advance, in particular dimension parameter values A of the examination object O and information about the type of imaging. The control signals are subsequently transmitted to the cited control interface 34. From there, the control signals AS are then relayed directly to the units involved in the imaging, such as, for example, the X-ray sources 15a, 15b, the X-ray detectors 16a, 16b, the patient couch 3, etc.

In addition, the schematic in FIG. 3 also shows a contrast agent injection device 35, via which the patient O can be injected with a contrast agent in advance, i.e. prior to the start of the CT imaging method. The improved contrast can then be used for determining the above-described virtual monoenergetic image data V-BD on the basis of a contrast agent image and a second basis material image, such as water or bone material, for example.

Most or all of the components of the image data generating device 20 can be realized in the form of software elements on a suitable processor. In particular, the interfaces between the components may also be embodied exclusively in software. Access to suitable storage areas in which the data can be suitably buffered and retrieved again and updated at any time may be provided.

FIG. 4 shows a typical image 40 of a coronal slice through a patient. The image is visualized here using a windowing scheme having a center of 60 HU and a window width of 400 HU, which corresponds to a lower threshold value of −140 HU and an upper threshold value of 260 HU. In this case it is principally the lung L, which can be seen at top left in the image and comprises low HU values, that is discernible in particular detail. The relatively air-rich tissue of the lung L having a particularly low density absorbs the X-ray beams relatively well at low energy, as a result of which these areas appear relatively bright. The kidneys N contain a lot of blood in their fine vessel structures and therefore also absorb much harder X-ray radiation. As can be seen in FIG. 4, the kidneys appear very bright in the image. The HU values of the kidneys are already very high at the first energy E1=45 keV, so they lie at the edge of the window chosen for a detailed visualization of the lungs L and, as it were, almost "knock against" the upper threshold of the window and are therefore visualized at maximum brightness. A lung window lies at X-ray attenuation values of −1000 HU to 200 HU, for example. The kidney window, in contrast, comprises values from approx. −120 HU to 240 HU and therefore lies just inside the range of the chosen windowing setting. A higher keV value E3=55 keV would be more favorable for a more detailed visualization of the kidneys N. Vessels and arteries contain a particularly large amount of blood with corresponding iodine-containing contrast agent and therefore absorb the X-ray radiation even more strongly than the kidneys N. A window between approx. −300 HU and 500 HU at 45 keV would be suitable for these. For these areas encompassed by the background H, an even higher keV value E3=65 keV is therefore suitable. If it is desired to visualize the bone framework comprising the hip joints HG and the spinal column WS, for which the upper window threshold lies at approx. 1300 HU and which is particularly dense and absorbs X-ray beams extremely strongly, then a keV value of E3=150 keV is suitable.

FIG. 5 shows a so-called target keV image 50 of the torso shown in FIG. 4. The target keV image 50 is subdivided into segments S1, S2, S3, S4. A first segment S1 shown at top left in FIG. 5 comprises the lung L and is suitable for a keV value of 45 keV. A second segment S2 on the right next to the first segment S1 is subdivided into two areas which include the kidneys N. A keV value of 55 keV is suitable for this second segment S2. A third segment S3 comprises the background H containing large blood vessels, for example, and is intended to be visualized at a keV value of 65 keV. A fourth segment S4 comprises the bone framework with the hip joints HG at bottom left and right in the image and the spinal column WS in the center of the image. This fourth segment S4 is now to be visualized at a keV value of 150 keV. The image shows a soft, unsharp transition between the segments S1, S2, S3, S4, which has been achieved by a lowpass filtering of the original organ mapping. The unsharp transitions are intended to indicate that virtual monoenergetic image data is generated in this area at keV values with continuous transitions in order to achieve a smooth transition between the individual segments S1, S2, S3, S4 in the subsequent overall image G-BD and reduce noise effects and artifacts.

Figure 6:
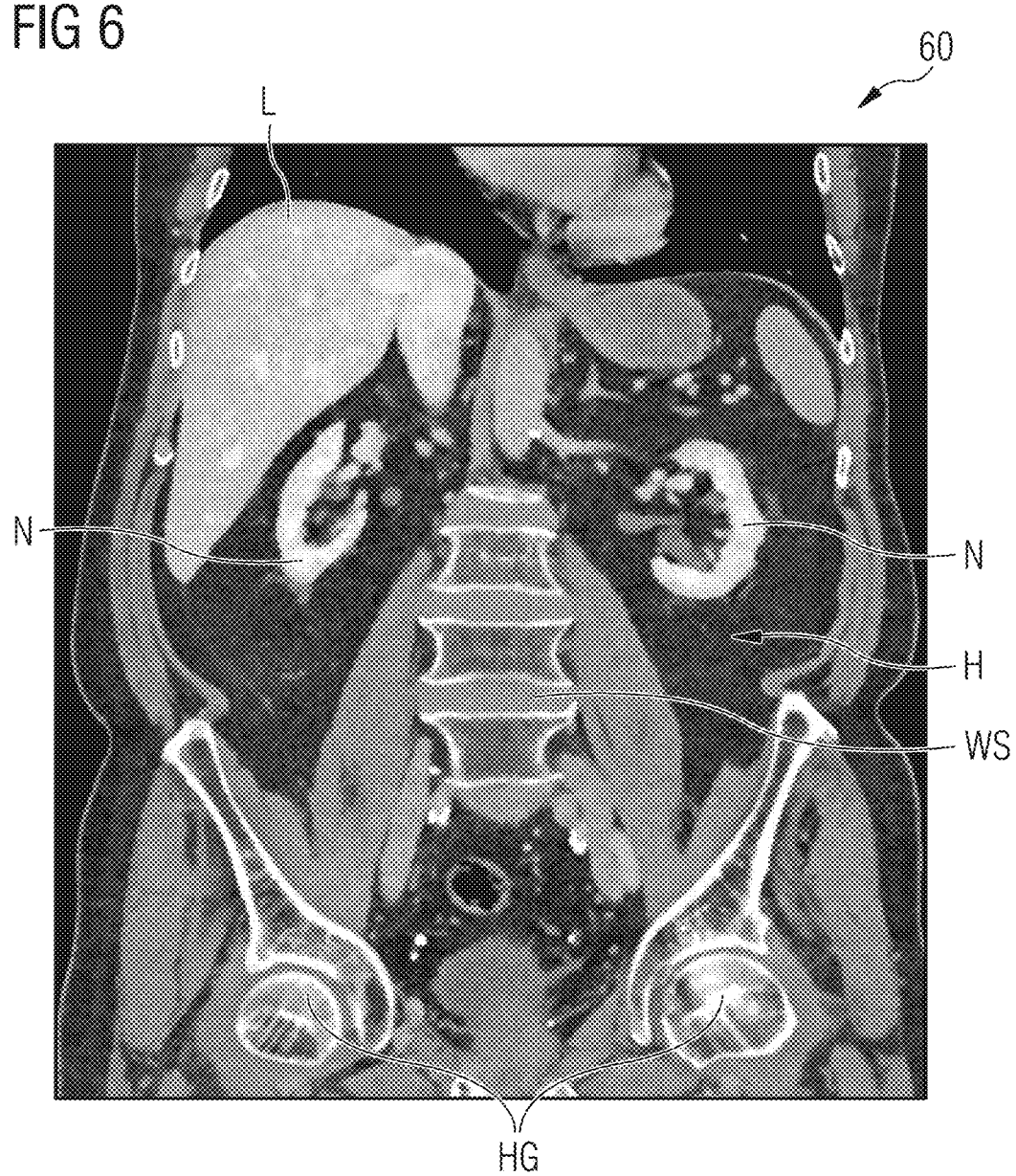
FIG. 6 shows an overall image generated by an X-ray imaging method according to at least one example embodiment.

FIG. 6 shows a view 60 of the torso already shown in FIG. 4, the depicted image being assembled from image areas having different organ-dependent keV weightings. The torso is visualized here throughout using the same windowing setting with a center of 60 HU and a window width of 400 HU, which corresponds to a lower threshold value of −140 HU and an upper threshold value of 260 HU.

In this case the lung L is once again shown at top left in the image and can be seen in particularly rich detail. The lung segment is visualized at a keV value of 45 keV. The relatively air-rich tissue of the lung having a particularly low density absorbs the X-ray beams relatively well at low energy, as a result of which these areas appear relatively bright. The kidneys N are visualized at a keV value of 55 keV, as a result of which they appear somewhat less bright and with somewhat more tissue structure. Furthermore, the background H is visualized at a keV value of 65 keV. This makes vessels more clearly recognizable in terms of their structure and dimensions.

The bone framework comprising the hip joints HG at bottom left and right in the image and also the spinal column WS in the center of the image is visualized at a keV value of 150 keV. Now, the structures in the bones are also much more clearly visible since artifacts are reduced as a result of the lower brightness and the HU value range of the uniformly specified windowing settings can be used more effectively for visualizing structures.

In conclusion it is pointed out once again that the methods and devices described in the foregoing are simply exemplary embodiments and that the example embodiments may be varied by the person skilled in the art without leaving the scope of the example embodiments, insofar as this is defined by the claims. Thus, the X-ray imaging method for generating image data of an examination region and the image data generating device have been explained primarily with reference to a system for the acquisition of medical image data. However, the example embodiments are not limited to an application in the field of medicine, but rather example embodiments may also be applied generally to the acquisition of images for other purposes. It is also pointed out for the sake of completeness that the use of the indefinite articles "a" or "an" does not exclude the possibility that the features in question may also be present more than once. Equally, the term "unit" does not rule out the possibility that this may consist of a plurality of components, which if necessary may also be spatially distributed.

The invention claimed is:

1. An X-ray imaging method for generating image data of an examination region of an object that is to be examined, said method comprising:

acquiring first X-ray projection measurement data of the examination region using a first X-ray energy spectrum and at least second X-ray projection measurement data of the examination region using a second X-ray energy spectrum which is different from the first X-ray energy spectrum;

reconstructing a priori image data on the basis of at least the first X-ray projection measurement data;

determining a location-dependent distribution of X-ray attenuation values in the examination region on the basis of the a priori image data;

performing a basis material decomposition on the basis of the first X-ray projection measurement data and the at least second X-ray projection measurement data;

determining a location-dependent weighting of the basis materials as a function of the location-dependent distribution of the X-ray attenuation values, wherein the determining the location-dependent weighting includes, determining a location-dependent third X-ray energy spectrum with a location-dependent third mean energy as a function of the determined location-dependent distribution of X-ray attenuation values, and determining the location-dependent weighting on the basis of the determined location-dependent third X-ray energy spectrum; and generating an overall image for the examination region by reconstructing virtual basis-material-weighted image data weighted differently depending on location.

2. The method as claimed in claim 1, wherein the location-dependent third X-ray energy spectrum comprises a single location-dependent third energy value in each case.

3. The method as claimed in claim 2, wherein the location-dependent third energy value is determined by applying a lookup table to the determined location-dependent distribution of X-ray attenuation values.

4. The method as claimed in claim 2, wherein the location-dependent third energy value is determined using a target function which maps X-ray attenuation values to suitable third energy values.

5. The method as claimed in claim 1, wherein
individual imaged organ regions are segmented and classified in the a priori image data,
a specific basis material weighting is specified in each case as a function of the different location-dependent distribution of the X-ray attenuation values in the different segments, and
virtual basis-material-weighted image data, weighted on a segment-specific basis in each case, is reconstructed for the overall image.

6. The method as claimed in claim 5, wherein the specific basis material weighting is determined as a function of the classification of the individual segments by organ types.

7. The method as claimed in claim 1, wherein the virtual basis-material-weighted image data is reconstructed as a function of spectral information of the a priori image data.

8. The method as claimed in claim 7, wherein the spectral information is used to identify materials foreign to the body and to specify a specific basis material weighting for reconstructing the virtual basis-material-weighted image data as a function of the identified materials.

9. The method as claimed in claim 5, wherein during the reconstruction of virtual basis-material-weighted image data, weighted on a segment-specific basis,
a third energy value is varied continuously depending on location in at least one segment, and
a continuous transition is produced in a border zone between at least two segments by approximation of the third energy values of the two segments to one another in the border zone.

10. The method as claimed in claim 1, wherein one of the following basis material decompositions is applied during the reconstruction of the virtual basis-material-weighted image data:
a material decomposition into iodine and water,
a material decomposition into iodine and bone, and
a combination of regionally different material decompositions for different segments of the examination region.

11. An image data generating device comprising:
a control unit for controlling one or more X-ray sources of a CT system in such a way that X-ray beams are generated using a first X-ray energy spectrum and a different second X-ray energy spectrum;
a projection measurement data acquisition unit for acquiring first X-ray projection measurement data of an examination region of an examination object using the first X-ray energy spectrum and at least second X-ray projection measurement data using the second X-ray energy spectrum;
a preliminary image reconstruction unit for reconstructing a priori image data on the basis of at least the first X-ray projection measurement data;
a value determination unit for determining a location-dependent distribution of X-ray attenuation values in the examination region on the basis of the first X-ray projection measurement data;
a decomposition unit for performing a basis material decomposition on the basis of the first X-ray projection measurement data and the at least second X-ray projection measurement data;
a weighting unit for determining a location-dependent weighting of the basis materials as a function of the location-dependent distribution of the X-ray attenuation values, wherein the weighting unit is configured to determine the location-dependent weighting by,
determining a location-dependent third X-ray energy spectrum with a location-dependent third mean energy as a function of the determined location-dependent distribution of X-ray attenuation values, and
determining the location-dependent weighting on the basis of the determined location-dependent third X-ray spectrum; and
an image generating unit for generating an overall image for the examination region by reconstructing virtual basis-material-weighted image data weighted differently depending on location.

12. A computed tomography system comprising an image data generating device as claimed in claim 11.

13. A non-transitory computer-readable medium on which program sections that are executable by a computer unit are stored in order to perform all the steps of the method as claimed in claim 1 when the program sections are executed by the computer unit.

14. The method as claimed in claim 2, wherein
individual imaged organ regions are segmented and classified in the a priori image data,
a specific basis material weighting is specified in each case as a function of the different location-dependent distribution of the X-ray attenuation values in the different segments, and virtual basis-material-weighted image data, weighted on a segment-specific basis in each case, is reconstructed for the overall image.

15. The method as claimed in claim 3, wherein individual imaged organ regions are segmented and classified in the a priori image data, a specific basis material weighting is specified in each case as a function of the different location-dependent distribution of the X-ray attenuation values in the different segments, and virtual basis-material-weighted image data, weighted on a segment-specific basis in each case, is reconstructed for the overall image.

16. An image data generating device comprising:

processing circuitry configured to, control one or more X-ray sources of a CT system in such a way that X-ray beams are generated using a first X-ray energy spectrum and a different second X-ray energy spectrum;

acquire first X-ray projection measurement data of an examination region of an examination object using the first X-ray energy spectrum and at least second X-ray projection measurement data using the second X-ray energy spectrum;

reconstruct a priori image data on the basis of at least the first X-ray projection measurement data;

determine a location-dependent distribution of X-ray attenuation values in the examination region on the basis of the first X-ray projection measurement data;

perform a basis material decomposition on the basis of the first X-ray projection measurement data and the at least second X-ray projection measurement data;

determine a location-dependent weighting of the basis materials as a function of the location-dependent distribution of the X-ray attenuation values, the processing circuitry configured to determine the location-dependent weighting by, determining a location-dependent third X-ray energy spectrum with a location-dependent third mean energy as a function of the determined location-dependent distribution of X-ray attenuation values, and determining the location dependent weighting on the basis of the determined location-dependent third X-ray energy spectrum; and generate an overall image for the examination region by reconstructing virtual basis-material-weighted image data weighted differently depending on location.

* * * * *